United States Patent [19]

Saulson et al.

[11] Patent Number: 4,530,368

[45] Date of Patent: Jul. 23, 1985

[54] TEMPORARY BIPOLAR PACING LEAD

[75] Inventors: Stanley H. Saulson, Miami; Walter H. Wesner, Plantation, both of Fla.

[73] Assignee: Cordis Corporation, Miami, Fla.

[21] Appl. No.: 613,586

[22] Filed: May 24, 1984

[51] Int. Cl.³ .............................................. A61N 1/04
[52] U.S. Cl. .................................. 128/784; 128/419 P
[58] Field of Search ..................... 128/419 P, 784-785

[56] References Cited

U.S. PATENT DOCUMENTS

| | | | |
|---|---|---|---|
| 3,244,174 | 4/1966 | Wesbey et al. | 128/418 |
| 3,333,045 | 7/1967 | Fisher et al. | 174/20 |
| 3,474,791 | 10/1969 | Bentov | 128/418 |
| 3,664,347 | 5/1972 | Harmjanz | 128/419 P |
| 4,144,889 | 3/1979 | Tyers et al. | 128/418 |
| 4,289,138 | 9/1981 | Halvorsen | 128/419 P |
| 4,338,947 | 7/1982 | Williams | 128/642 |
| 4,341,226 | 7/1982 | Peters | 128/419 P |
| 4,442,840 | 4/1984 | Wojciechowicz, Jr. | 128/419 P |
| 4,444,207 | 4/1984 | Robicsek | 128/785 |

Primary Examiner—William E. Kamm
Attorney, Agent, or Firm—Henry W. Collins; Thomas R. Vigil

[57] ABSTRACT

The bipolar temporary pacing lead comprises a lead body having a proximal end portion and a distal end portion and including first and second spaced apart wire conductors each encased in an insulating material to form insulated wire conductors. A curved needle is connected to at least one of the first and second wire conductors in the lead body distal end portion. A straight needle is connected to a first elongate non-conductive member and a second elongate non-conductive member which are connected by means of first and second terminal sleeves to proximal ends of the first and second wire conductors. The distal end portion of the lead body has insulation removed from portions of the respective first and second insulated conductors thereby to form in the lead body distal end portion a first electrode-forming, bare wire conductor portion and a second electrode-forming, bare wire conductor portion.

11 Claims, 1 Drawing Figure

TEMPORARY BIPOLAR PACING LEAD

FIELD OF THE INVENTION

The present invention relates to a temporary bipolar pacing lead which is adapted to be mounted to a myocardium of a heart.

DESCRIPTION OF THE PRIOR ART

Heretofore, various devices have been proposed for fixing a pacing lead to heart tissue by making an incision through the chest wall and then implanting an electrode within the myocardium of the heart by threading the electrode through the epicardium into the myocardium of the heart wall. Examples of some of the previously proposed body implantable electrodes are disclosed in the following U.S. Patents:

| U.S. PAT. NO. | PATENTEE |
| --- | --- |
| 3,244,174 | Wesbey et al. |
| 3,474,791 | Bentov |
| 4,144,889 | Tyres et al. |
| 4,338,947 | Williams et al. |

The prior temporary electrode devices disclosed in the above identified patents have utilized single conductors with each conductor having a separate curved needle at the end thereof for insertion into (for threading the electrode portion through) heart tissue, such as the epicardium, to implant an exposed portion (electrode) of the lead within the myocardium of the heart.

Often it is desired to place two such electrodes in the heart to provide for bipolar pacing and then to supply an electrical signal through one wire conductor to an electrode fixed to the myocardium so that the signal can pass through the myocardium causing the heart muscle to be dully polarized and contract and then return by the second electrode and the wire conductor connected thereto to a pacer having a pulse generator therein.

To provide such a bipolar system two separate leads were utilized, each having a curved needle at the distal end thereof and a percutaneous straight needle at the proximal end thereof.

To simplify the procedure for implanting the two electrodes in a heart wall, it has been proposed to construct a bipolar temporary pacing lead having a single lead body with a proximal end portion and a distal end portion and including first and second spaced apart wire conductors each encased in an insulating material to form insulated wire conductors. A straight needle is connected to the proximal end portion of the lead body, namely to the proximal ends of both wire conductors. The proximal end portion of each wire conductor has a terminal connector sleeve crimped thereon. A curved needle is connected at the distal end of the lead body to one or both of the insulated wire conductors. Insulation is removed from spaced apart portions of respective first and second insulated conductors in the distal end portion of the lead body to form in the lead body distal end portion a first electrode-forming, bare wire conductor portion and a second electrode-forming, bare wire conductor portion.

In such pacing lead, one of the wire conductors in the distal end portion of the lead body can be broken so that there is no short circuit between the two wire conductors at their connection to the curved needle and so that, once the curved needle is cut away, there is no electrical path through body fluids between the cut wire conductor ends. However, the two wire conductors are shorted to each other at their connection to the straight needle and excess proximal end portions of the wire conductors are cut away.

With the previously proposed temporary bipolar pacing lead construction, once the electrode forming portions have been threaded into the heart and the straight needle brought out through the chest wall, the needles, and adjacent portions of the wire conductors, are cut away.

A drawback with this construction is that if the position of the electrode-forming, bare wire conductor end portions is not satisfactory, and both needles had to be cut away, it is then necessary to remove the lead and implant a new lead. This is because at least the straight needle has to be cut away in order that the wire conductors are not shorted when an electrical connection is made to the respective terminal connector sleeves mounted on the respective proximal end portions of each of the insulated wire conductors.

As will be described in greater detail hereinafter, the temporary bipolar pacing lead of the present invention differs from the previously proposed bipolar pacing leads by providing first and second elongate non-conductive members connected respectively between the straight needle and the respective proximal ends of the first and second insulative wire conductors. This way, once the lead is implanted, neither of the needles has to be cut away in order for a pulse generator to be connected to the terminal sleeve connectors for testing the placement of the electrodes in the myocardium.

SUMMARY OF THE INVENTION

According to the invention there is provided a bipolar temporary pacing lead comprising a lead body having a proximal end portion and a distal end portion, and including first and second spaced apart wire conductors each having a proximal end and a distal end and each being encased in an insulating material to form insulated wire conductors, a curved needle, at least one of said first and second wire conductors in said lead body distal end portion being connected to said curved needle, a straight needle, a first elongate non-conductive member and a second elongate non-conductive member, the proximal end of each of said elongate non-conductive members being connected to said straight needle, first means for connecting said first elongate non-conductive member to a proximal end of said first wire conductor and second means for connecting said second elongate non-conductive member to a proximal end of said second wire conductor, and said distal end portion of said lead body having insulation removed from portions of said respective first and second insulated conductors thereby to form in said lead body distal end portion a first electrode-forming, bare wire conductor portion and a second electrode-forming, bare wire conductor portion.

DESCRIPTION OF THE PREFERRED EMBODIMENT

Figure 1:
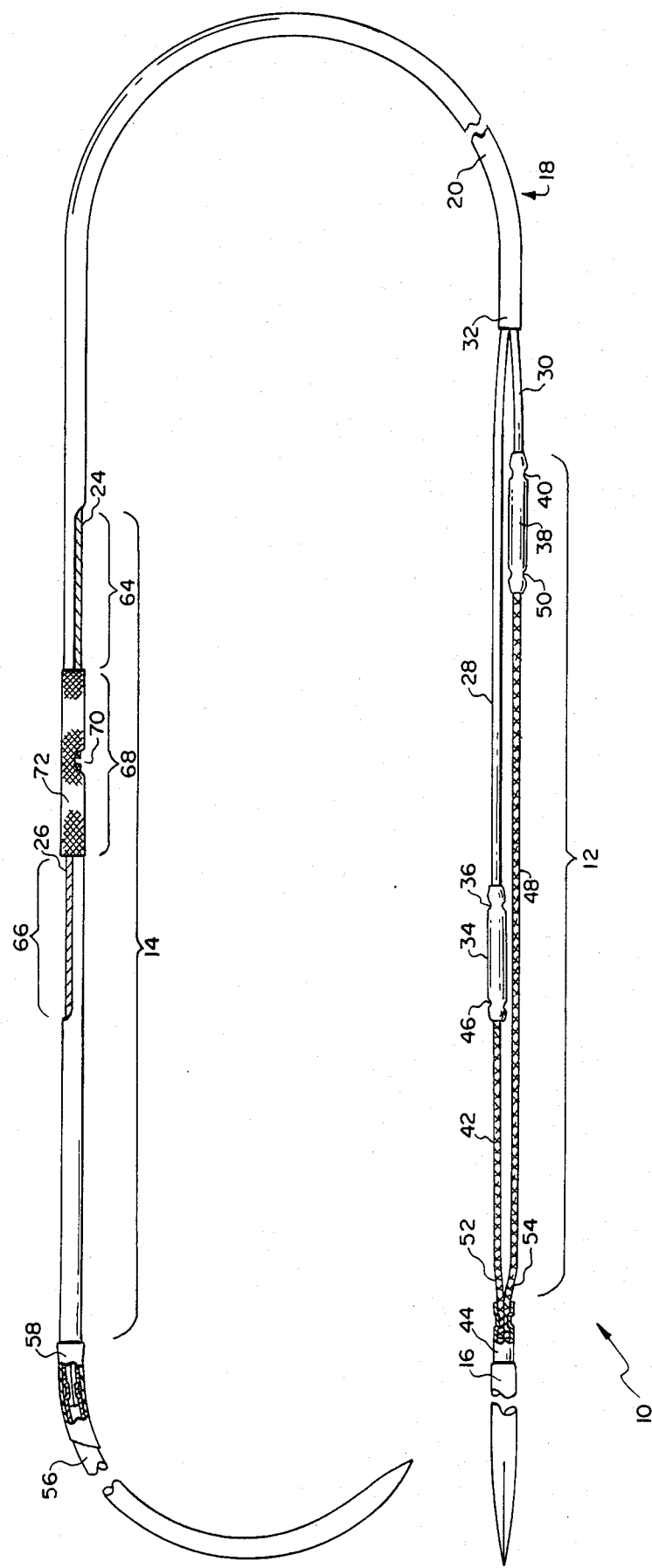
FIG. 1, is a plan view of the temporary bipolar pacing lead of the present invention, including a lead body with a curved needle at the distal end thereof and a straight needle at the proximal end thereof connected by first and second non-conductive elongate members to the proximal ends of wire conductors in the lead body.

Referring now to the single FIGURE, FIG. 1, there is illustrated therein a temporary bipolar pacing lead which is generally identified by reference numeral 10. As shown, the pacing lead 10 has a proximal end portion 12 and a distal end portion 14. Connected to the proximal end portion 12 is a conventional straight needle 16.

As shown, the lead 10 includes a body 18 comprising a sheath 20 and two insulated wire conductors 24 and 26 having an outer layer 28, 30 of insulating material thereon. The insulated wire conductors 24, 26 are received within the sheath 20.

As shown, the proximal end 32 of the sheath 20 ends just before the proximal end 12 of the lead body 18 such that the insulated conductors 24 and 26 with insulation 28, 30 thereon extend rearwardly from the proximal end 32 of the sheath 20 toward the straight needle 16.

The conductor 24 insulated within the coating or sleeve of insulation 28 extends further back from the end 32 of the sheath 20 than does the insulated conductor 26 and into a stainless steel terminal connector sleeve 34. After removing about 2 mm of insulation 28 from the proximal end of conductor 24, it is inserted into connector sleeve 34, and the sleeve 34 is crimped, as shown at 36, thereby making electrical contact between them. The insulated conductor 26 with insulation 30 thereon extends from the end 32 of the sheath 20 a shorter distance than the conductor 24 and into a second stainless steel terminal connector sleeve 38 which has a crimp 40 therein for crimping through the insulation 30 and into contact with the conductor 26.

Then, according to the teachings of the present invention, a first non-conductive elongate member 42 extends from a hollow or cavity (not shown) in one end 44 of the needle 16 to and into the other end of the stainless steel connector sleeve 34 which is crimped at 46 onto the member 42. In like manner, a second, longer, elongate non-conductive member 48 extends from the hollow or cavity in the end 44 of the needle 16 to and into the terminal connector sleeve 38 which is then crimped at 50 onto the non-conductive member to securely grip the elongate non-conductive member 48.

Proximal ends 52 and 54 of the non-conductive members 42 and 48, respectively, are both received in the hollow or cavity in the end 44 of the needle 16 which is then crimped to secure the proximal ends of 52 and 54 of the non-conductive members to needle 16.

The non-conductive members 42 and 48 are typically monofilaments such as nylon monofilaments. As will be described in greater detail hereinafter, the use of non-conductive nylon monofilaments for coupling the straight needle 16 to the terminal connector sleeves 34 and 36 results in no short circuit between the conductors 24 and 26 at the needle 16.

As shown, the distal end portion 14 of the lead body 18 is connected to a curved needle 56. Typically the distal ends of the insulated conductors 24 and 26 with or without insulation thereon are received in a cavity or hollow in an end 58 of the curved needle 56 which is then crimped onto the wire conductors 24 and 26 to secure them firmly to the end 58 of the curved needle 56.

A portion 64 of the insulated conductor 24 has insulation removed to provide a bare wire conductor portion 64 at the beginning of the distal end portion 14. Then spaced from that portion 64 is a portion 66 of the insulated wire conductor 26 which has the insulation removed therefrom to expose or bare the wire conductor 26. These two portions 64 and 66 define electrode-forming, bare wire conductor portions 64 and 66 of the insulated wire conductors 24 and 26.

A portion 68 of the lead body 18 is situated between the electrode-forming, bare wire conductor portions 64 and 66. In the section 68, the insulated wire conductor 24 is broken as indicated at break 70 so that there is a space of approximately 0.05 inch between the separated ends of the wire conductor 24 in the break 70. This section 68 then has a colored sleeve 72 received thereover to cover the broken wire conductor 24 at the break 70 and to provide a marker on the lead body 18.

As a result of the break 70 and the provision of the nylon monofilaments 42 and 48, the wire conductors 26 and 24 are isolated and insulated from each other and are not shorted to each other at either the distal end portion 14 or the proximal end portion 12 of the lead body 18.

This construction of the lead 10 with the wire conductors 24 and 26 isolated or insulated from each other provides greater flexibility in the use of the lead 10. In this respect, in use, a physician takes two bites with the needle 56 into the myocardium or heart wall of a heart to place both electrode-forming, bare wire conductor portions 64 and 66 within the myocardium with the colored sleeve 72 exposed on the outside of the heart. The colored sleeve 72 then indicates that both wire conductor portions are embedded within the heart wall.

The physician brings the straight needle 16 out of the chest wall where test leads (not shown) from a pulse generating circuit can be attached to the terminal sleeve connectors 34 and 38 respectively, such as by use of so-called alligator clips at the ends of the test leads. Then pulses can be supplied through the pulse generator leads and the terminal connector sleeves 34 and 38 to the wire conductors 24 and 26 so that heart stimulating pulses can be supplied to the heart via the electrode-forming, bare wire conductor portions 64 and 66.

Then, if the testing by the physician indicates that good electrical contact has been made between the electrode-forming bare wire conductor portions 64 and 66 in the heart wall or myocardium of the heart (not shown) the physician can cut away the needle 56 and a portion of the lead body 18 in the distal end portion 14 extending from the heart wall. Likewise the monofilaments 42 and 48 can be cut adjacent the proximal ends of the terminal connector sleeves 34 and 38 and the connector sleeves 34 and 38 can then be inserted into appropriate sockets of an adapter connected to a pacemaker or directly to the pacemaker.

It will be appreciated that with the lead end constructed with monofilaments 42 and 48 as described above, tests can be made without cutting away the needles 16 and 56 such that if good electrical connection is not made between the electrode-forming, bare wire conductor portions 64 and 66 and the heart wall, the physician does not have to discard the lead 10 and obtain a new lead 10. Instead, the physician merely can thread the needle 56 backwardly through the first and second bites in the heart wall and then the needle 56 can be used by the physician for making two new bites or threadings through the heart wall to place the electrode-forming, bare wire conductor portions 64 and 66 in better electrical connection with the heart wall.

From the foregoing description it will be appreciated that the lead 10 of the present invention has a number of advantages, some of which have been described above and others of which are inherent in the invention. Also modifications can be made to the lead 10 without departing from the teachings of the present invention. Accordingly, the scope of the invention is only to be limited as necessitated by the accompanying claims.

I claim:

1. A bipolar temporary pacing lead comprising a lead body having a proximal end portion and a distal end portion, and including first and second spaced apart wire conductors each having a proximal end and a distal end and each being encased in an insulating material to form insulated wire conductors, a curved needle, at least one of said first and second wire conductors in said lead body distal end portion being connected to said curved needle, a straight neelde, a first elongate non-conductive member and a second elongate non-conductive member, the proximal end of each of said elongate non-conductive member being connected to said straight needle, first means for connecting said first elongate non-conductive member to a proximal end of said first wire conductor and second means for connecting said second elongate non-conductive member to a proximal end of said second wire conductor, and said distal end portion of said lead body having insulation removed from portions of said respective first and second insulated conductors thereby to form in said lead body distal end portion a first electrode-forming, bare wire conductor portion and a second electrode-forming, bare wire conductor portion.

2. The pacing lead of claim 1 wherein said first and second non-conductive members are defined by first and second lengths of monofilament.

3. The pacing lead of claim 2 wherein each length of monofilament is made of nylon.

4. The pacing lead of claim 1 wherein said second non-conductive members is longer than said first non-conductive member.

5. The pacing lead of claim 1 wherein said first and second means for connecting said respective first and second non-conductive members to said respective first and second conductors, each comprise a metal terminal connector sleeve with a first crimp in each sleeve over a distal end of one of the non-conductive members and a second crimp in the sleeve over a proximal end of one of the wire conductors.

6. The pacing lead of claim 5 wherein said second crimp is over a portion of said wire conductor from which insulation has been removed to make a good electrical contact with the wire condcutor therein.

7. The pacing lead of claim 5 wherein said sleeves are made of stainless steel.

8. The pacing lead of claim 1 wherein said first and second insulated wire conductors are received in a sheath which extends from the curved needle rearwardly to a point before the connection of one of said wire conductors to one of said elongate non-conductive members.

9. The pacing lead of claim 1 wherein siad sheath in a distal end portion thereof has portions cut away to expose a portion of said first and second insulated conductors and each exposed portion of said insulated wire conductors has the insulation thereon removed so as to form said electrode-forming, bare wire conductor portions.

10. The pacing lead of claim 9 including a sleeve, having a color different than the color of said sheath, positioned over said sheath between said first and second electrode-forming, bare wire conductor portions.

11. The pacing lead of claim 10 wherein both of said insulated wire conductors are connected to said curved needle and said first wire conductor is broken with the portion of said wire conductors covered by said colored sleeve.

* * * * *

UNITED STATES PATENT AND TRADEMARK OFFICE
CERTIFICATE OF CORRECTION

PATENT NO.   : 4,530,368
DATED        : July 23, 1985
INVENTOR(S)  : Stanley H. Saulson It is certified that error appears in the above-identified patent and that said Letters Patent is hereby corrected as shown below:

Column 2, line 63, "FIGURE" should be --figure--.
         line 63, "FIG. 1," should be --Fig. 1--.
Column 3, line 4, "FIGURE" should be --figure--.
         line 4, "FIG. 1," should be --Fig. 1--.
         line 11, insert "lead" after --a--.
Column 4, line 45, after "electrode-forming" insert a comma.
Column 5, line 1, "foregoining" should be --foregoing--.
         line 10, "claim" should be --Claim--.
         line 19, Claim 1, "neelde" should be --needle--.
Column 6, line 15, Claim 6, "condcutor" should be --conductor--.
         line 24, Claim 9, "siad" should be --said--.

Signed and Sealed this

Twenty-ninth Day of April 1986

[SEAL]

Attest:

DONALD J. QUIGG

Attesting Officer

Commissioner of Patents and Trademarks